United States Patent [19]
Armstrong

[11] Patent Number: 5,772,692
[45] Date of Patent: Jun. 30, 1998

[54] IMPLANTABLE MEDICAL DEVICE WITH AUTOMATIC ADJUSTMENT TO EXTERNALLY GENERATED SHOCKS

[75] Inventor: Randolph K. Armstrong, Missouri City, Tex.

[73] Assignee: Sulzer Intermedics Inc., Angleton, Tex.

[21] Appl. No.: 739,267

[22] Filed: Oct. 29, 1996

[51] Int. Cl.⁶ .................................................. A61N 1/18
[52] U.S. Cl. ............................................. 607/11; 607/7
[58] Field of Search ................................. 607/4, 5, 6, 7, 607/8, 11, 13

[56] References Cited

U.S. PATENT DOCUMENTS 3,805,795  4/1974  Denniston et al. ......................... 607/6
4,300,567  11/1981  Kolenik et al. .............................. 607/5
5,314,448  5/1994  Kroll et al. ................................. 607/5
5,318,591  6/1994  Causey, III et al. ........................ 607/5

Primary Examiner—William E. Kamm
Attorney, Agent, or Firm—John R. Merkling

[57]     ABSTRACT

An implantable cardiac stimulator, which may include cardioversion and pacemaker capabilities, which has apparatus for detecting an externally applied shock, such as a defibrillation or cardioverting shock. In response to detection of such a shock, the cardiac stimulator has apparatus to adjust the parameters of applied therapy, or to select alternative therapy, including, but not limited to, adjusting the magnitude of stimulus pulses for a predetermined length of time. The risk of loss of capture, and consequent failure of cardiac function, following an externally applied shock is thereby reduced.

15 Claims, 3 Drawing Sheets

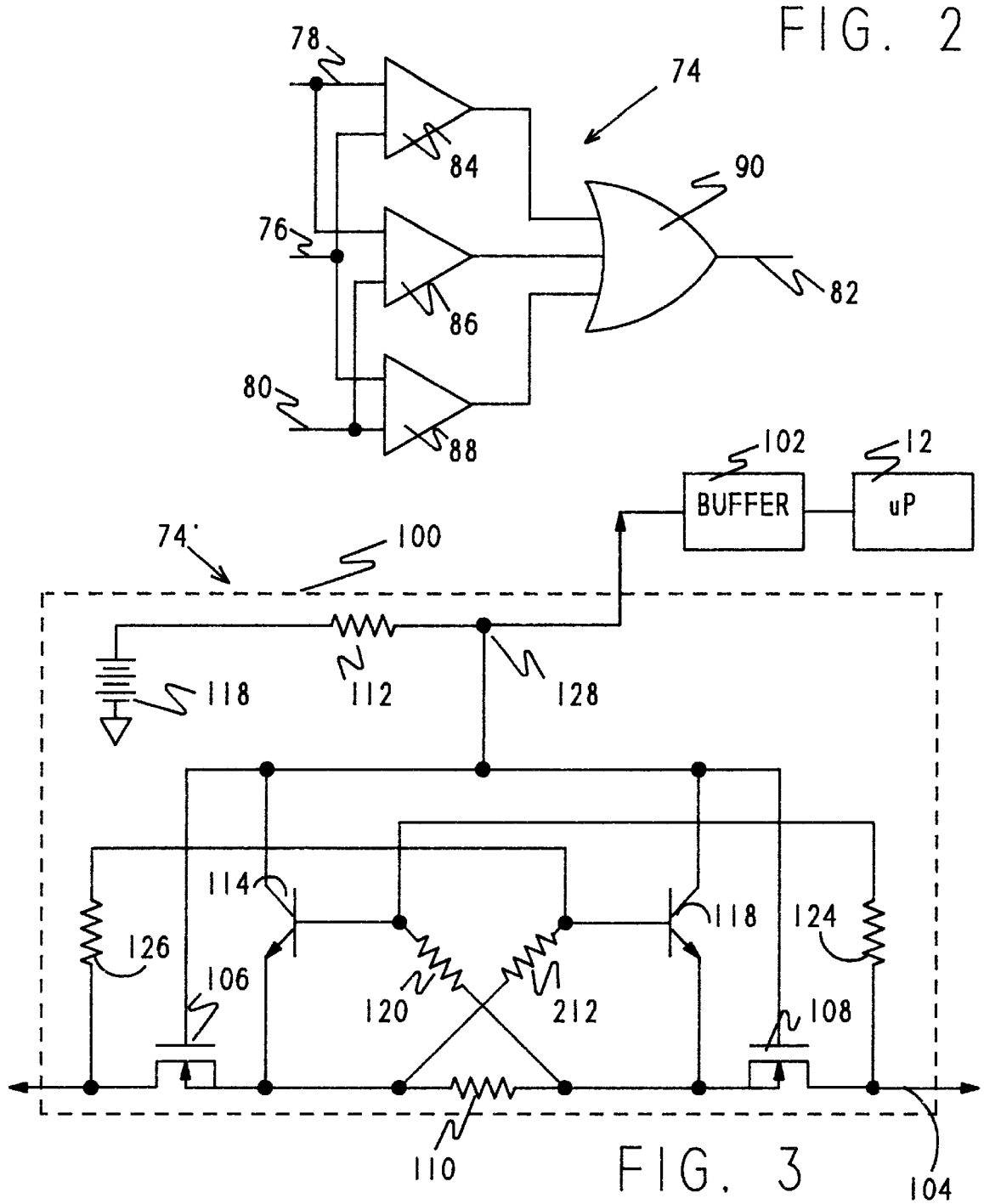

5,772,692

IMPLANTABLE MEDICAL DEVICE WITH AUTOMATIC ADJUSTMENT TO EXTERNALLY GENERATED SHOCKS

FIELD OF MY INVENTION

My invention is directed towards an implantable cardiac stimulator such as a cardiac pacemaker or a cardioverter-defibrillator, incorporating a circuit for detecting an externally applied shock and for resetting the stimulation parameters in response thereto, in particular, for temporarily increasing the magnitude of a stimulation pulse to avoid loss of capture.

BACKGROUND OF MY INVENTION

The basic implantable cardioverter/defibrillator or pacemaker system consists of at least one electrode attached to the heart and connected by a flexible lead to a pulse generator. This generator is a combination of a power source and the microelectronics required for the system to perform its intended function. A fixed rate pacemaker provides continuous pulses to the heart, irrespective of proper heart beating, while a demand inhibited pacemaker 15 provides pulses only when the heart fails to deliver a natural pulse. Depending upon the various sensed events, the pacemaker stimulates the right atrium, the right ventricle, or both chambers of the heart in succession. The pacemakers in current use incorporate circuits and antennae to communicate non-invasively with external instruments called programmers. Most of today's pacemakers are of the demand inhibited type, hermetically sealed, and programmable.

Implantable cardioverters/defibrillators add the capability of correcting dangerous arrhythmias and fibrillation by selected stimulation patterns or high energy shocks. High energy shocks are used primarily to correct life-threatening fibrillations by essentially stopping the heart and allowing an appropriate rhythm to re-establish itself.

External defibrillation is used for the termination of various atrial and ventricular tachyarrythmias. This therapy may be applied to pacemaker patients, including patients who are pacemaker dependent. It has been found that application of external shocks may produce transient loss of capture, that is, the stimulation threshold of the patient appears to be affected at least temporarily, and an implanted pacemaker may no longer adequately cause contractions of the heart. This phenomenon is directly related to the magnitude and number of applied shocks. Although the threshold may gradually recover, usually within minutes, the phenomenon has been observed to extend for hours. In pacemaker dependent patients, even the transient loss of capture for three or four minutes may be life threatening. It has been suggested, by Altamura et al., "Transthoracic DC Shock May Represent a Serious Hazard in Pacemaker Dependent Patients" PACE, volume 18, Jan. 1995, pages 194–198, that the likelihood of capture failure could be reduced by programming the highest possible stimulation energy of a permanent pacemaker before a shock. This suggestion assumes the availability of the appropriate pacemaker programmer, and may not be practical in emergency situations, particularly in cases of ventricular fibrillation where the application of large defibrillation shocks are most likely.

Implantable defibrillators, which automatically deliver a cardioverting shock under appropriate circumstances, may also include a cardiac pacemaker. Such devices can provide circuitry and software to adapt the cardiac pacemaking functions in the event of the application of an internally generated shock. However, current pacemakers and current cardioverter defibrillators do not provide means for recognizing the application of an external shock and taking the appropriate measures to avoid loss of capture. There remains a need, therefore, for an implantable cardiac stimulator which can recognize the application of external shocks, such as defibrillation shocks.

There also remains a need for an implantable cardiac stimulator which, upon recognition of an externally applied shock, takes appropriate action to avoid loss of capture or to otherwise vary the applied therapy.

SUMMARY OF MY INVENTION

I have invented an implantable cardiac stimulator, which may include cardioversion and pacemaker capabilities, which has apparatus for detecting an externally applied shock, such as a defibrillation or cardioverting shock. In response to detection of such a shock, a cardiac stimulator of my invention has apparatus to adjust the parameters of applied therapy, or to select alternative therapy, including, but not limited to, adjusting the magnitude of stimulus pulses for a predetermined length of time. The risk of loss of capture, and consequent failure of cardiac function, following an externally applied shock is thereby reduced.

I will now describe my preferred embodiment of my invention, in connection with the accompanying drawings.

BRIEF DESCRIPTION OF THE DRAWINGS

FIG. 2 is a block diagram of a shock detector.

FIG. 3 is a block diagram of an alternative shock detector.

DESCRIPTION OF MY PREFERRED EMBODIMENT

Figure 1:
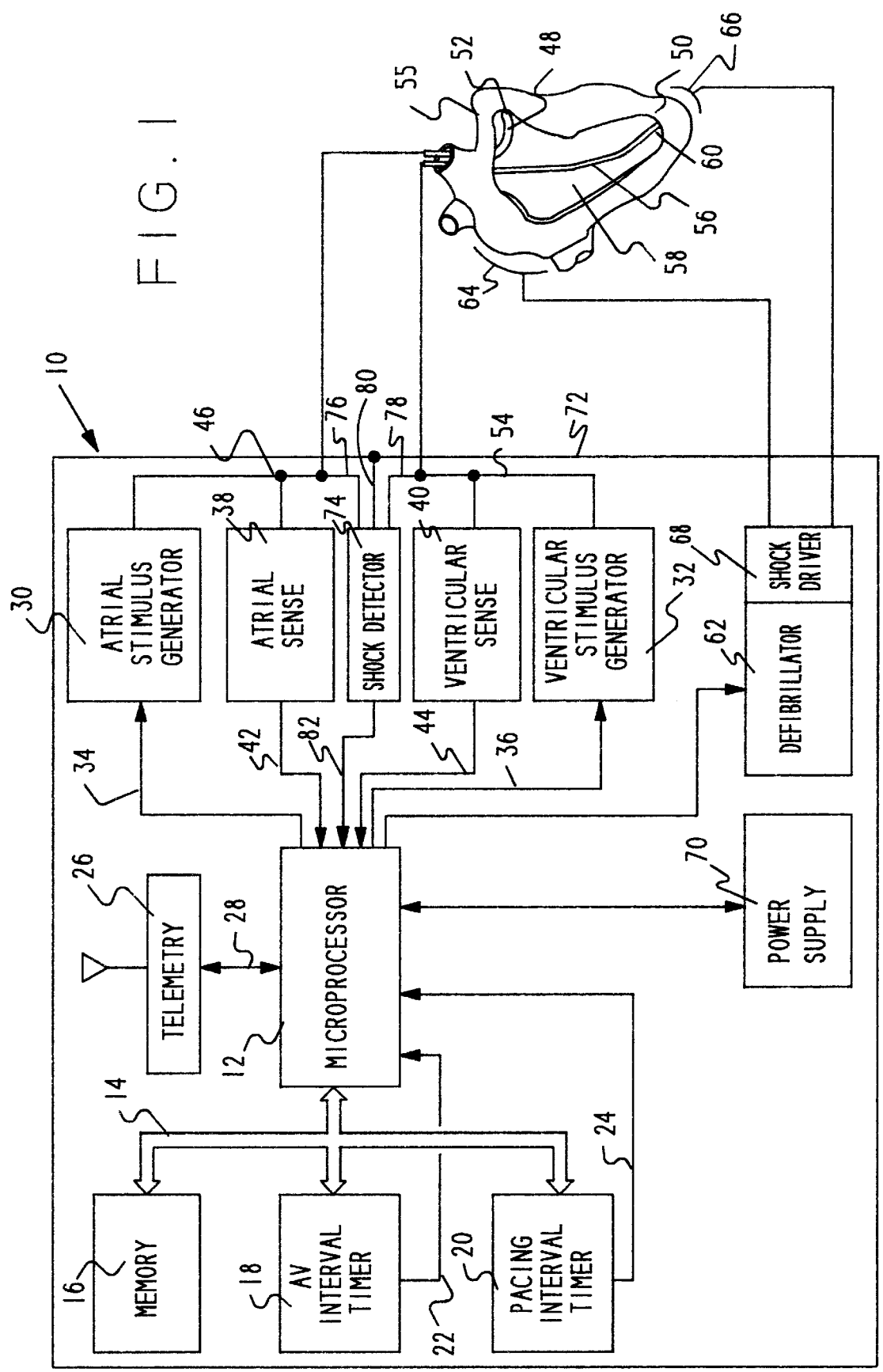
FIG. 1 is a block diagram of an implantable cardiac stimulator.

FIG. 1 is a block diagram illustrating a cardiac stimulator 10 according to my invention. A microprocessor 12 preferably provides pacemaker control and computational facilities. It will be appreciated that other forms of circuitry, such as analog or discrete digital circuitry can be used in place of microprocessor 12. However, a microprocessor is preferred for its miniature size and its flexibility, both of which are of critical importance in the implantable systems in which it is envisioned the invention will find use. A particularly energy efficient microprocessor which is designed specifically for use with implantable medical devices is fully described in Gordon, et al, U.S. Pat. No. 4,404,972, which is also assigned to my assignee and the disclosure thereof is incorporated herein by reference.

The microprocessor 12 has input/output ports connected in a conventional manner via bidirectional bus 14 to a memory 16, an A-V interval timer 18, and a pacing interval timer 20. In addition, the A-V interval timer 18 and pacing interval timer 20 each has an output connected individually to a corresponding input port of the microprocessor 12 by lines 22 and 24 respectively. The A-V and pacing interval timers 18 and 20 may be external to the microprocessor 12, as illustrated, or internal thereto, as described in Gordon, et al U.S. Pat. No. 4,404,972. The timers 18, 20 are suitable conventional up or down counters of the type that are initially loaded with a count value and count up to or down from the value and output a roll-over bit upon completing the programmed count. The initial count value is loaded into the timers 18, 20 on bus 14 and the respective roll-over bits are output to the microprocessor 12 on lines 22, 24.

Memory 16 preferably includes both ROM and RAM. The microprocessor 12 may also contain additional ROM and RAM as described in Gordon, et al., mentioned above. The pacemaker operating routine is stored in ROM. The RAM stores various programmable parameters and variables. The microprocessor 12 preferably also has an input/output port connected to a telemetry interface 26 by line 28. The pacemaker when implanted is thus able to receive pacing, arrhythmia therapy, and rate control parameters from an external programmer and send data to an external receiver if desired. Many suitable telemetry systems are known to those skilled in the art. One such system and encoding arrangement is described in Armstrong et al., U.S. Pat. No. 5,383,912 which is also assigned to my assignee. That description is incorporated herein by reference.

The microprocessor 12 output ports are connected to inputs of an atrial stimulus pulse generator 30 and a ventricular stimulus pulse generator 32 by control lines 34 and 36 respectively. The microprocessor 12 transmits pulse parameter data, such as amplitude and width, as well as enable/disable and pulse initiation codes to the generators 30, 32 on the respective control lines. The microprocessor 12 also has input ports connected to outputs of an atrial sense amplifier 38 and a ventricular sense amplifier 40 by lines 42 and 44 respectively. The atrial and ventricular sense amplifiers 38, 40 detect occurrences of P-waves and R-waves. The atrial sense amplifier 30 outputs a signal on line 42 to the microprocessor 12 when it detects a P-wave. This signal is latched to the microprocessor 12 input port by a conventional latch (not shown). The ventricular sense amplifier 40 outputs a signal on line 44 to the microprocessor 12 when it detects an R-wave. This signal is also latched to the microprocessor 12 input port by a conventional latch (not shown).

The input of the atrial sense amplifier 38 and the output of the atrial stimulus pulse generator 30 are connected to a first conductor 46, which passes through a conventional first lead 48. Lead 48 is inserted into a patient's heart 50 intravenously or in any other suitable manner. The lead 48 has an electrically conductive pacing/sensing tip 52 or tip and ring at its distal end which is electrically connected to the conductor 46. The pacing/sensing tip 52 is preferably lodged in the right atrium 55. The input of the ventricular sense amplifier 40 and the output of the ventricular stimulus pulse generator 32 are connected to a second conductor 54. The second conductor 54 passes through a conventional second lead 56 which is inserted intravenously or otherwise in the right ventricle 58 of the heart 50. The second lead 56 has an electrically conductive pacing/sensing tip 60 or tip and ring at its distal end. The pacing/sensing tip 60 is electrically connected to the conductor 54. The pacing/sensing tip 60 is preferably lodged on the wall of the right ventricle 58.

The conductors 46, 54 conduct the stimulus pulses generated by the atrial and ventricular stimulus pulse generators 30, 32 respectively, to the pacing/sensing tips 52, 60. The pacing/sensing tips 52, 60 and corresponding conductors 46, 54 also conduct cardiac electrical signals sensed in the right atrium and right ventricle to the atrial and ventricular amplifiers, 38, 40 respectively. The sense amplifiers 38, 40 enhance the electrical signals. In the preferred embodiments of my invention, the amplifiers 38, 40 have an automatic gain control feature, as described in U.S. Pat. No. 4,903,699 to Baker, et al. That patent is assigned to the same assignee as my present invention, and the disclosure thereof is incorporated herein by reference.

The implantable cardiac stimulator 10 also has a defibrillator circuit 62. If fibrillation is detected through the atrial or ventricular sense amplifiers 38, 40, a high energy shock can be delivered through defibrillation leads and electrodes 64, 66. Detection algorithms for detection of tachycardias and fibrillation are described in Pless, et al, U.S. Pat. No. 4,880,005, incorporated herein by reference. Although patch-type electrodes are suggested by the drawing, endocardial electrodes for defibrillation are also known. The shock is controlled by a shock driver circuit 68. In the preferred embodiment of my invention, I consider it desirable to produce multi-phasic shocks for defibrillation through the shock driver 68. Circuitry particularly well adapted for producing such wave forms is described in detail in U.S. Pat. No. 4,800,883 to Winstrom, the disclosure of which is incorporated herein by reference. It will be understood, however, that my invention can be employed with monophasic pulse generators and with pulse generators incorporating multiphasic stimulation.

All of the aforementioned components are powered by a power supply 70. The power supply 70 may comprise either standard or rechargeable batteries or both, which may be dedicated to the operation of different parts of the stimulator 10. The electronic components heretofore described are all preferably contained within a hermetically sealed can 72. The can may serve as an indifferent electrode in so called "unipolar" operation. Alternatively, a dedicated electrode may be provided on one or both of the leads 48, 56, or at another location, for so called "bipolar" operation.

In accordance with my invention, a shock detector 74 is provided to identify externally applied shocks which produce an electrical field with a potential greater than or equal to a preselected voltage. The shock detector 74 is preferably connected to one or more of the electrodes of the system. For example, the shock detector 74 may be connected to the atrial electrode 52 through the atrial lead 48 and to the ventricular electrode 60 through the ventricular lead 56. The shock detector may also be connected to the indifferent electrode, which may comprise the can 72 as illustrated in FIG. 1. The shock detector 74 provides a signal to the microprocessor 12 over a line 82 whenever a shock is detected. The microprocessor 12 responds by adjusting selected operating parameters of the cardiac stimulator 10, including, preferably, the magnitude of any stimulation pulses being applied to either the atrium or the ventricle or both by the atrial stimulus generator 30 or the ventricular stimulus generator 32 respectively. Preferably, the output of the generators 30, 32 should be temporarily adjusted to maximum for a predetermined period of time.

A first embodiment of the shock detector 74 is illustrated in greater detail in FIG. 2. In this first embodiment, the shock detector 74 comprises a bank of differential amplifiers 84, 86, 88 and an OR gate 90. At least two electrodes are needed to detect the applied external shock. Preferably, more than two electrodes would be employed so that a propagating field could be more reliably detected. If a field propagates perpendicular to a line between two electrodes, for example, a very small electrical gradient would be detected. With multiple electrodes, there is less likelihood that a field would not be detected by at least one electrode pair. In the illustrated embodiment, three electrodes are selected: the atrial electrode 52, the ventricular electrode 60 and the can 72. The first differential amplifier 84 is connected between the ventricular electrode through line 78 and the atrial electrode through line 76. The second differential amplifier 86 is connected between the ventricular electrode through line 78 and the can through line 80. Third differential amplifier 88 is connected across the atrial electrode through line 76 and the can through line 80. Each of the differential amplifiers is set to produce a positive output in the presence of a voltage difference of greater than a preselected magnitude, for example, 10 volts. The outputs of each of the differential amplifiers 84, 86, 88 are connected to OR gate 90. The OR gate 90 produces a high output on the occurrence of a signal from any of the differential amplifiers or any combination thereof. This output is conducted from the OR gate 90 along line 82 to the microprocessor. The OR gate logically combines the outputs of the differential amplifiers. This function could also be performed by other apparatus. For example, the microprocessor itself could be programmed to accept input from all the amplifiers, and to respond to any or all of the amplifiers. The differential amplifiers and the OR gate also function to buffer the microprocessor 12 from the effects of a high-voltage signal so that the voltage is not conducted directly to the microprocessor, which could damage the microprocessor.

A second embodiment 74' of the shock detector is illustrated in FIG. 3. Shock detector 74' involves a modification of a protection circuit described by Winstrom in U.S. Pat. No. 4,745,923, incorporated herein by reference. The shock detector 74' comprises the protection circuit 100 connected through a voltage clamp or buffer 102 to the microprocessor 12. The protection circuit 100 is electrically connected to an electrode, such as electrode 60, by an electrical conductor 104. In series with the conductor 104 are a first and a second field effect transistor (FET), 106,108 and a sensing resister 110. The drain of the second FET 108 connects to the conductor 104. The source of the second FET 108 connects to one side of the sensing resistor 110 and the source of the first FET 106 connects to the opposite end. The drain of the first FET 106 connects to the opposite end of the conductor 104 which is connected to the pacemaker circuitry, such as the atrial sense amplifier 38. The gates of the first and second FET 106, 108 are connected in parallel to one end of a current limiting resistor 112 and to the collectors to first and second parallel bipolar transistors 114,116. The other end of the current limiting resistor 112 connects to a DC voltage source 118.

The emitter of the first bipolar transistor 114 connects to the source of the first FET 106. The emitter of the second bipolar transistor 116 connects to the source of the second FET 108. A first resistor 120 connects to the base of the first bipolar transistor 114 with the emitter of the second bipolar transistor 116. Likewise, a second resistor 122 connects the base of the second bipolar transistor 116 with the emitter of the first bipolar transistor 114. The base of the first bipolar transistor 114 also connects to the drain.of the second FET 108 through a resistor 124. Likewise the base of the second bipolar transistor 116 connects to the drain of the first FET 106 through a second resister 126.

The operation of the protection circuit 100 described above is extensively explained in the Winstrom '923 patent. As explained therein, the application of a large voltage, above a preselected value, such as may be experienced during the application of a defibrillating shock by either an implanted or an external defibrillator, causes a high impedance path to be activated. This path comprises the resistor 126,122,110, and the second FET 108 for negative pulses. During normal operation, that is, in the absence of a large voltage, the voltage at node 128 adjacent the current limiting resistor 112 will normally be high, that is, in the range of five to nine volts with respect to reference ground. In the presence of an external high voltage, the voltage at node 128 will drop to approximately 0.7 volts. This feature may be utilized as a logic signal with low-true whenever a shock is detected. A voltage limiting circuit 102 may be provided to limit the high-false condition if the microprocessor 12 will not tolerate the full potential of the voltage source 118. The microprocessor may use the low-true signal as an input to interrupt the software processing to begin a post shock response. Alternatively, if the microprocessor does not utilize interrupts, the signal could be feed to a sense latch input to set a condition true until the microprocessor 12 queries that input.

Figure 4:
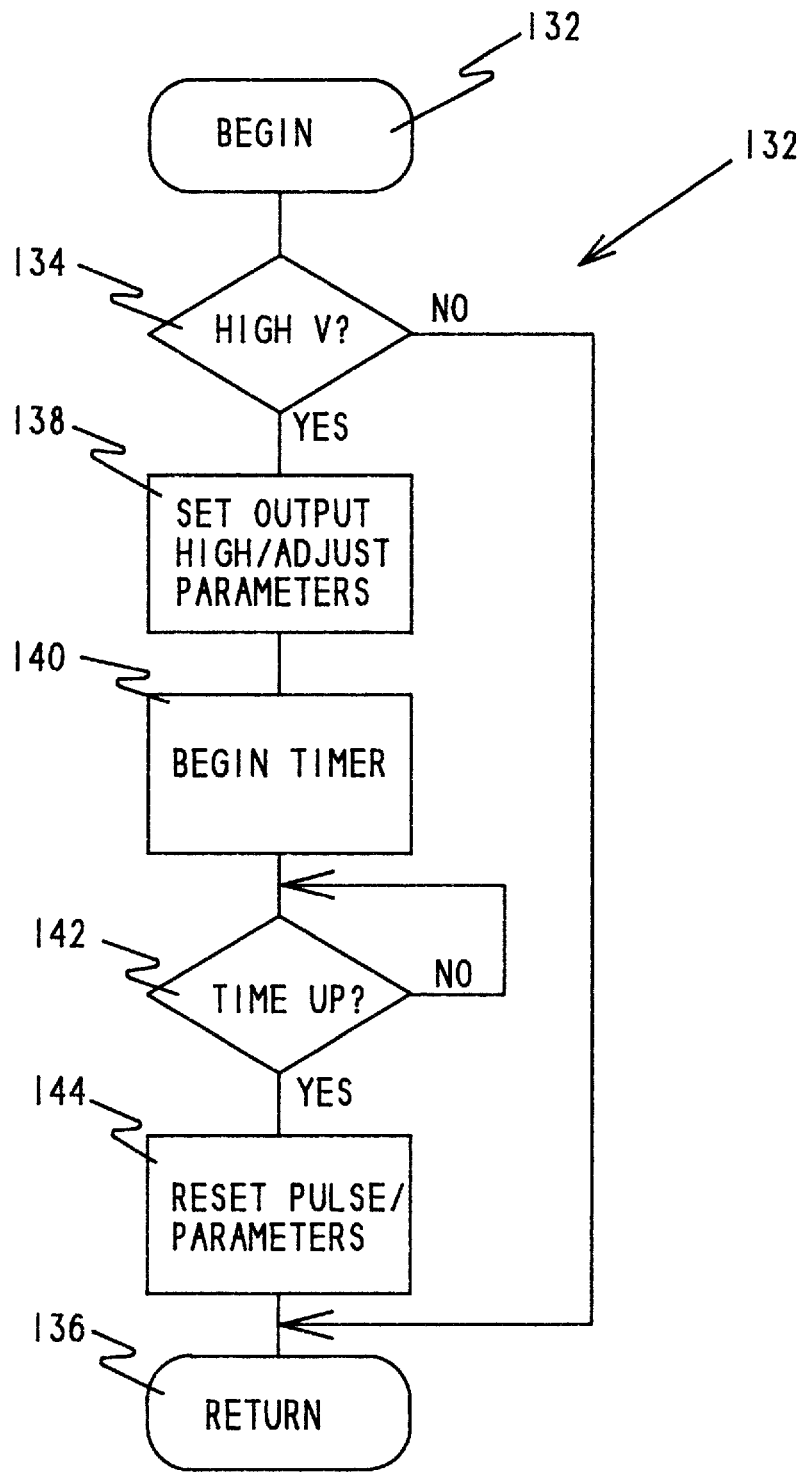
FIG. 4 is a flow chart for adjusting pulse parameters.

In the microprocessor 12, a portion of the programming is devoted to response to detected high voltage, as illustrated in FIG. 4. A program segment 130 begins 132 periodically during the operation of the software. If a high voltage condition is not detected 134, the programming returns at 136 to the balance of the pacemaker' programming. If the high voltage condition is detected through the shock detector circuit 74, the microprocessor 12 adjusts its parameters 138. This may involve selection of alternative therapies, adjustment of sense amplifier sensitivities, or other parameters. Most particularly, however, the pacemaker output pulse should be increased, and preferably set at or near maximum available pulse output to assure capture during a vulnerable period immediately following a shock. A timer 140 should be initiated to time out a preselected period of time for the application of the post shock response. The microprocessor 12 will then check for the expiration of the preselected time 142 and, when the time has elapsed, reset 144 the output and other parameters previously in operation before the detection of the shock.

While a preferred embodiment of my invention has been described above, it will be apparent to those skilled in the art from consideration of the disclosure herein that various modifications could be implemented without departing from the principles of my invention. Accordingly, it is intended that the scope of my invention be limited only by the appended claims.

I claim as my invention:

1. An implantable cardiac stimulator comprising a hermetically sealed container;

a battery within said container;

a control circuit connected to said battery for providing a stimulating electrical pulse to the heart;

means coupled to said control circuit for delivering said stimulating pulse to the heart;

a detector for detecting the presence of an externally generated electrical shock;

an adjustment circuit responsive to said detector for causing said control circuit to increase the magnitude of said stimulating electrical pulse.

2. The implantable cardiac stimulator according to claim 1 further comprising a timer for maintaining the increased magnitude of said stimulating electrical pulse for a preselected time after detection of said electric shock.

3. The implantable cardiac stimulator according to claim 1 wherein said means for delivering said stimulating pulse comprises a lead and an electrode carried on said lead and in electrical communication with said control circuit and an indifferent electrode and wherein said adjustment circuit comprises a differential amplifier connected between said electrode and said indifferent electrode.

4. The implantable cardiac stimulator according to claim 3 further comprising a plurality of electrodes and a plurality of differential amplifiers, a differential amplifier being connected between each pair of two electrodes and between each electrode and said indifferent electrode, and an OR gate, the output of each differential amplifier being connected to an input of said OR gate, and the output of said OR gate being connected to said control circuit.

5. The implantable cardiac stimulator according to claim 3 further comprising a plurality of electrodes and a plurality of differential amplifiers, a differential amplifier being connected between each pair of two electrodes and between each electrode and said indifferent electrode, and means for logically responding to at least one of the outputs of said differential amplifiers.

6. The implantable cardiac stimulator according to claim 3 wherein said indifferent electrode is on said container.

7. The implantable cardiac stimulator according to claim 3 wherein said indifferent electrode is located on a lead.

8. The implantable cardiac stimulator according to claim 3 wherein said control circuit further comprises a cardiac pacemaker.

9. The implantable cardiac stimulator according to claim 3 wherein said control circuit further comprises a cardioverter/defibrillator.

10. The implantable cardiac stimulator according to claim 3 further comprising a timer for maintaining the increased magnitude of said stimulating electrical pulse for a preselected time after detection of said electric shock.

11. The implantable cardiac stimulator according to claim 1 wherein said adjustment circuit comprises
    a circuit coupled to said means for delivering said stimulating pulse for protecting said cardiac stimulator against excessive electrical currents and
    a buffer coupled to said protecting means and to said control circuit and activated whenever said protective circuit responds to an excessive electrical current.

12. The implantable cardiac stimulator according to claim 11 wherein said protective circuit comprises
    means connected to form an electrically conductive low-impedance path for connection in circuit with said pulse delivering means;
    means connected to form an electrically conductive high-impedance path for connection in circuit with said pulse delivering means;
    means for generating a signal representative of the current flowing in said low-impedance path;
    switch means for opening and closing said low-impedance path; and
    means responsive to said signal representative of said current for controlling said switch means to open said low-impedance path when said current exceeds a predetermined level so that said current flows in said high impedance path.

13. The implantable cardiac stimulator according to claim 11 wherein said control circuit further comprises a cardiac pacemaker.

14. The implantable cardiac stimulator according to claim 11 wherein said control circuit further comprises a cardioverter/defibrillator.

15. The implantable cardiac stimulator according to claim 11 further comprising a timer for maintaining the increased magnitude of said stimulating electrical pulse for a preselected time after detection of said electric shock.

* * * * *